(12) United States Patent
Nishiguchi et al.

(10) Patent No.: US 9,090,529 B1
(45) Date of Patent: Jul. 28, 2015

(54) METHOD FOR PRODUCING 1,2-DICHLORO-3,3,3-TRIFLUOROPROPENE

(71) Applicant: CENTRAL GLASS COMPANY, LIMITED, Ube, Yamaguchi (JP)

(72) Inventors: Yoshio Nishiguchi, Kawagoe (JP); Satoru Okamoto, Kawagoe (JP); Fuyuhiko Sakyu, Kawagoe (JP)

(73) Assignee: CENTRAL GLASS COMPANY, LIMITED, Ube, Yamaguchi (JP)

( * ) Notice: Subject to any disclaimer, the term of this patent is extended or adjusted under 35 U.S.C. 154(b) by 0 days.

(21) Appl. No.: 14/663,400

(22) Filed: Mar. 19, 2015

Related U.S. Application Data

(63) Continuation of application No. PCT/JP2013/075541, filed on Sep. 20, 2013.

(30) Foreign Application Priority Data

Sep. 21, 2012 (JP) ................................. 2012-207929

(51) Int. Cl.
 *C07C 17/25* (2006.01)
 *C07C 17/23* (2006.01)

(52) U.S. Cl.
 CPC ................ *C07C 17/25* (2013.01); *C07C 17/23* (2013.01)

(58) Field of Classification Search
 CPC ............................... C07C 17/25; C07C 17/23
 USPC ................................................ 570/156, 157
 See application file for complete search history.

(56) References Cited

U.S. PATENT DOCUMENTS

| | | | |
|---|---|---|---|
| 6,369,284 | B1 | 4/2002 | Nappa et al. |
| 2005/0090698 | A1 | 4/2005 | Merkel et al. |
| 2005/0119512 | A1 | 6/2005 | Du Boisson et al. |

FOREIGN PATENT DOCUMENTS

| | | |
|---|---|---|
| JP | H09-67281 A | 3/1997 |
| JP | 2001-509803 A | 7/2001 |
| JP | 2006-193437 A | 7/2006 |
| JP | 2006-525339 A | 11/2006 |
| JP | 2008-110980 A | 5/2008 |
| JP | 2012-020992 A | 2/2012 |

OTHER PUBLICATIONS

International Search Report issued on Oct. 29, 2013 regarding PCT application No. PCT/JP2013/075541.
Written Opinion of the International Searching Authority issued on Oct. 29, 2013 regarding PCT application No. PCT/JP2013/075541.
Albert L. Henne, et al., A New Method of Synthesizing Organic 1,1,1-Trifluorides, 1941, Journal of the American Chemical Society, 1941, vol. 63, p. 3478-3479.
A. M. Whaley et al., Isomerization During Allylic Fluorination, 1948, Journal of the American Chemical Society, 1948, vol. 70, p. 1026-1027.
R. N. Haszeldine, Reactions of Fluorocarbon Radicals. Part V. Alternative Synthesis for Trifluoromethylacetylene (3:3:3-Trifluoropropyne), and the Influence of Polyfluoro-groups on Adjacent Hydrogen and Halogen Atoms, Journal of the Chemical Society, 1951, p. 2495-2504.

*Primary Examiner* — Elvis O Price
(74) *Attorney, Agent, or Firm* — Lowe Hauptman & Ham, LLP

(57) ABSTRACT

The present invention has an object of providing a method for producing 1,2-dichloro-3,3,3-trifluoropropene by a vapor-phase reaction easily and in an industrial scale. A method for producing 1,2-dichloro-3,3,3-trifluoropropene of the present invention includes putting 1,2-dichloro-1-halogeno-3,3,3-trifluoropropane with an activated carbon catalyst in a vapor phase. According to the present invention, 1,2-dichloro-3,3,3-trifluoropropene is produced in an industrial scale at a high yield by use of 1,2-dichloro-1-halogeno-3,3,3-trifluoropropane, which is available at low cost, as a material.

4 Claims, No Drawings

METHOD FOR PRODUCING 1,2-DICHLORO-3,3,3-TRIFLUOROPROPENE

CROSS REFERENCE TO RELATED APPLICATIONS

This application is based upon and claims the benefit of priority from the prior Japanese Patent Application No. 2012-207929, filed on Sep. 21, 2012, and PCT Application No. PCT/JP2013/075541, filed on Sep. 20, 2013, the entire contents of which are incorporated herein by reference.

FIELD

The present invention relates to a method for producing 1,2-dichloro-3,3,3-trifluoropropene.

BACKGROUND 1,2-dichloro-3,3,3-trifluoropropene includes an unsaturated bond, and is expected to provide a function of a cleaner or a coolant as hydrochlorofluorocarbon (HCFC), which is relatively easily decomposed in the atmosphere.

There are various known methods for producing 1,2-dichloro-3,3,3-trifluoropropene. For example, A. L. Henne et al., J. Am. Chem. Soc., 1941, pp. 3478-3479 discloses a method of reacting 1,2,3,3,3-pentachloropropene with antimony trifluoride in a liquid-phase.

A. M. Whaley et al., J. Am. Chem. Soc., 1948, pp. 1026-1027 discloses a method of reacting 1,1,2,3,3-pentachloropropene with antimony trifluoride in a liquid phase by adding antimony pentachloride. R. N. Haszeldine et al., J. Chem. Soc., 1951, pp 2495-2504 discloses a method of adding potassium hydroxide in a solid state to 1,2,2,-trichloro-3,3,3-trifluoropropane in a liquid state and refluxing, while heating, the resultant substance to produce 1,2-dichloro-3,3,3-trifluoropropene.

Regarding a vapor-phase reaction, Japanese Laid-Open Patent Publication No. 2012-20992 discloses a method of producing a fluorine-containing propene represented by general formula, $CF_3CH=CHZ$ (Z is Cl or F), by a fluorination reaction and a dehalogenation reaction by use of a chlorine-containing compound as a material. In Example 4, it is described that 1,2-dichloro-3,3,3-trifluoropropene is generated as a byproduct of a fluorination reaction and a dehalogenation reaction of 1,1,1,3,3-pentachloropropane (240 fa).

According to the production method described in R. N. Haszeldine et al., J. Chem. Soc., 1951, pp 2495-2504, powdery potassium hydroxide is dispersed in 1,2,2-trichloro-3,3,3-trifluoropropane in a liquid state to cause a reaction. However, the yield is low (48%) and the reaction is not uniform. Therefore, this method is not considered to be efficient as an industrial production method.

As described in Japanese Laid-Open Patent Publication No. 2012-20992, it is known that 1,2-dichloro-3,3,3-trifluoropropene is generated by a fluorination reaction and a dehalogenation reaction of a chlorine-containing compound such as 1,1,1,3,3-pentachloropropane or the like in a vapor phase. However, it is difficult to obtain 1,2-dichloro-3,3,3-trifluoropropene in an industrially sufficient amount.

As can be seen from the above, it has been desired to establish a method for producing 1,2-dichloro-3,3,3-trifluoropropene, which is a target compound of the present invention, easily and in an industrial scale.

SUMMARY

The present invention has an object of providing a method for producing 1,2-dichloro-3,3,3-trifluoropropene by a vapor-phase reaction easily and in an industrial scale.

As a result of accumulating active studies to solve the above-described problems, the present inventors found that 1,2-dichloro-3,3,3-trifluoropropene, which is a target compound, is obtained at a high yield by putting 1,2-dichloro-1-halogeno-3,3,3-trifluoropropane into contact with an activated carbon catalyst in a vapor phase.

Namely, the present invention includes inventions 1 through invention 4 described below.

[Invention 1]

A method for producing 1,2-dichloro-3,3,3-trifluoropropene, including: putting 1,2-dichloro-1-halogeno-3,3,3-trifluoropropane represented by formula [1] below into contact with an activated carbon catalyst in a vapor phase:

[Chemical Formula 1]

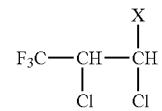

[1]

(in the formula, X represents fluorine, chlorine or bromine).

According to the element of invention 1, 1,2-dichloro-3,3,3-trifluoropropene is selectively generated while generation of a byproduct is suppressed. Thus, 1,2-dichloro-3,3,3-trifluoropropene can be obtained at a high yield.

[Invention 2]

A method according to invention 1, wherein the activated carbon catalyst is formed of activated carbon having no metal material supported thereon. Herein, the "carbon having no metal material supported thereon" refers to an activated carbon catalyst containing a metal material at a content in the range that is lower than or equal to 0.01% by mass including zero (0).

According to the element of invention 2, 1,2-dichloro-3,3,3-trifluoropropene can be obtained at a higher yield.

[Invention 3]

A method according to invention 1 or 2, wherein the 1,2-dichloro-1-halogeno-3,3,3-trifluoropropane is in contact with the activated carbon catalyst for a time that is longer than or equal to 1 second and shorter than or equal to 300 seconds, and at a temperature that is higher than or equal to 200° C. and lower than or equal to 350° C.

According to the element of invention 3, 1,2-dichloro-3,3,3-trifluoropropene can be obtained at a higher yield.

[Invention 4]

A method according to any one of inventions 1 through 3, wherein the 1,2-dichloro-1-halogeno-3,3,3-trifluoropropane is 1,1,2-trichloro-3,3,3-trifluoropropane.

According to the element of invention 4, 1,2-dichloro-3,3,3-trifluoropropene can be obtained at a higher yield.

DESCRIPTION OF EMBODIMENTS

Hereinafter, the present invention will be described in detail. In a reaction according to present invention, 1,2-dichloro-1-halogeno-3,3,3-trifluoropropane is put into contact with an activated carbon catalyst in a vapor phase to cause dehydrochlorination. Specifically, this reaction is caused by filling a reactor with an activated carbon catalyst and putting 1,2-dichloro-1-halogeno-3,3,3-trifluoropropane into contact with the activated carbon catalyst in a vapor phase at a predetermined temperature. The vapor-phase reaction may be a fixed-bed vapor-phase reaction, a fluidized-bed vapor-phase reaction or of any other appropriate system. Selection of any system of the vapor-phase reaction does not prevent a person of ordinary skill in the art from easily adjusting the reaction conditions.

1,2-dichloro-1-halogeno-3,3,3-trifluoropropane, which is a starting material of the present invention, is represented by formula [1].

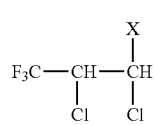

[1]

In formula [1], "X" specifically represents fluorine, chlorine or bromine. Specific compounds usable as 1,2-dichloro-1-halogeno-3,3,3-trifluoropropane include 1,1,2-trichloro-3,3,3-trifluoropropane, 1,2-dichloro-1,3,3,3-tetrafluoropropane, and 1-bromo-1,2-dichloro-3,3,3-trifluoropropane. Among these compounds, 1,1,2-trichloro-3,3,3-trifluoropropane is preferably usable for easy availability thereof and usefulness of a resultant compound.

Activated carbon catalysts include plant-based catalysts formed of wood, charcoal, palm shell charcoal, palm kernel charcoal, pure ash or the like; coal-based catalysts formed of peat, lignite, brown coal, bituminous coal, anthracite coal or the like; petroleum-based catalysts formed of petroleum residue, oil carbon or the like; or synthetic resin-based catalysts such as carbonized poly(vinylidene chloride) or the like. As the activated carbon catalyst used in the present invention, any of such commercially available activated carbon catalysts may be selected. Preferably usable activated carbon catalysts include, for example, palm shell charcoals for gas purification or for catalyst/catalyst support (Granulated Shirasagi GX, SX, CX and XRC produced by Japan EnviroChemicals, Ltd.; PCB produced by Toyo Calgon; Yashicoal produced by Taihei Chemical Industrial Co, Ltd.; and Kuraray Coal GG and GC) and the like. For the activated carbon catalyst according to the present invention, activated carbon having a metal material supported thereon or activated carbon having no metal material supported thereon may be used. Activated carbon having no metal material supported thereon is advantageous from the viewpoint of costs and ease of abolishment. In the present invention, the "carbon having no metal material supported thereon" refers to an activated carbon catalyst containing a metal material at a content that is at least 0 and lower than or equal to 0.01% by mass.

In the case where activated carbon having a metal material supported thereon is used, the supported metal material may be aluminum, chromium, titanium, manganese, iron, nickel, cobalt, copper, magnesium, zirconium, molybdenum, zinc, tin, lanthanum, antimony or the like. Such a metal material may be supported in the form of fluoride, chloride, fluorochloride, oxyfluoride, oxychloride, oxyfluorochloride, or the like. A combination of two or more of metal compounds may be supported.

The activated carbon catalyst is usually used in the form of granules, but may be used in a usually set form that is compatible to the reactor, such as spheres, fibers, powders, honeycomb-like components or the like. The specific surface area and the pore capacity of the activated carbon may be in the range of the standards for the commercially available products. The specific surface area is preferably larger than 400 $m^2/g$, and more preferably larger than or equal to 800 $m^2/g$ and smaller than or equal to 3000 $m^2/g$. The pore capacity is preferably larger than 0.1 $cm^3/g$, and more preferably larger than or equal to 0.2 $cm^3/g$ and smaller than or equal to 1.0 $cm^3/g$.

The reaction temperature for the present invention is usually higher than or equal to 200° C. and lower than or equal to 350° C., and preferably higher than or equal to 220° C. and lower than or equal to 320° C. When the reaction temperature is lower than 200° C., the reaction does not advance almost at all or the reaction is extremely slow, which is not preferable. When the reaction temperature is higher than 350° C., the decomposition reaction or the like advances and the resultant product may possibly be contaminated with a large amount of byproducts, which is not preferable.

In this specification, the term "contact time" is defined as follows. The "volume of the filler (activated carbon)" is set as A. The "volume of the material gas that is introduced into the reactor per second" is set as "B". Considering that the material gas is ideal gas, the value of B is calculated from the molar number per second and the pressure of the introduced material and nitrogen and the temperature. A value obtained by dividing A with B (=A/B) is referred to as the "contact time". In the reactor, HCl or other types of gas is produced as a byproduct and thus the molar number is changed. Such a change in the molar number is not considered for calculation of the "contact time".

The contact time varies in accordance with the temperature of the reactor (reaction temperature), the shape of the reactor, and the type of filler in the reactor. Therefore, it is desirable to adjust the supply rate of the material (contact time) for each of set temperatures, each of shapes of the reactor, and each of types of fillers, so that an optimal value is determined as the contact time. Usually, the contact time is preferably set such that a conversion rate of the material of at least 25% is obtained and is more preferably set such that a conversion rate of the material of at least 50% is obtained, from the viewpoint of recoverability and recyclability of an unreacted part of the material.

In a preferable example, in the case where the reaction temperature is kept in the range that is higher than or equal to 200° C. and lower than or equal to 350° C., the contact time is preferably longer than or equal to 1 second and shorter than or equal to 300 seconds, and more preferably longer than or equal to 20 seconds second and shorter than or equal to 150 seconds. When the contact time exceeds 300 seconds, a side reaction is easily caused, which is not preferable. When the contact time is shorter than 1 second, the conversion rate is too low, which is not preferable. In one preferable embodiment, 1,2-dichloro-1-halogeno-3,3,3-trifluoropropane is caused to pass the reactor, filled with activated carbon heated to a temperature that is higher than or equal to 200° C. and lower than or equal to 350° C., with a contact time that is longer than or equal to 1 second and shorter than or equal to 300 seconds.

The reaction pressure may be lower than, equal to, or higher than the atmospheric pressure. In general, the reaction pressure is preferably the atmospheric pressure. The reaction may be caused in the presence of inert gas such as nitrogen, argon or the like, which is stable under the reaction conditions.

The dehydrochlorination reaction according to the present invention may be caused in a vapor phase by use of a common chemical engineering device. A reactor, a related material introduction system, a flow-out system, and a related unit are formed of a substance that is durable against hydrogen chloride. Typical such substances include, for example, stainless steel, especially austenite-type stainless steel; high nickel alloys such as Monel™, Hastelloy™, Inconel™ and the like; and copper-clad steel, but are not limited to these.

1,2-dichloro-3,3,3-trifluoropropene produced by the method according to the present invention exists in the form of a liquid at room temperature and normal pressure. The gas obtained by the reaction may be caused to flow in a cooled condenser to be condensed, and precision-distilled, so that highly pure 1,2-dichloro-3,3,3-trifluoropropene is obtained. 1,2-dichloro-3,3,3-trifluoropropene generated by the reaction is a mixture of geometric isomers such as cis and trans isomers. Nonetheless, the mixture can be precision-distilled to provide highly pure cis-1,2-dichloro-3,3,3-trifluoropropene and trans-1,2-dichloro-3,3,3-trifluoropropene.

The cis isomer and the trans isomer can be mutually converted by an isomerization reaction. There is no specific limitation on the method of isomerization. The isomerization may be caused by a known vapor-phase reaction using a solid acid catalyst such as fluorinated alumina, fluorinated chromia, fluorinated titania, fluorinated zirconia or the like.

Hereinafter, the present invention will be described in more detail by way of examples. The present invention is not limited to the following examples. Herein, "%" used for a composition analysis value represents the "surface area %" of each of components of a reaction mixture measured by direct use of gas chromatography (unless otherwise specified, the detector is FID).

[Example 1]

Example 1 will be described hereinafter. In example 1, 1,2-dichloro-3,3,3-trifluoropropene was synthesized by use of activated carbon having no metal material supported thereon as a catalyst. Table 1 shows the synthesis results of 1,2-dichloro-3,3,3-trifluoropropene.

(Synthesis of 1,2-dichloro-3,3,3-trifluoropropene)

Nitrogen was caused to flow, at a rate of 10 ml/min., into a vapor-phase reaction device (formed of SUS304, inner diameter: 25 mm; length: 300 mm) formed of a cylindrical reactor equipped with a metal electric heater filled with 50 ml of granulated activated carbon (Shirasagi G2x; produced by Japan EnviroChemicals, Ltd.; specific surface area: 1200 m$^2$/g; pore capacity: 0.86 cm$^3$/g), while the temperature of the reactor was gradually raised. When the temperature of the reactor reached 250° C., 1,1,2-trichloro-3,3,3-trifluoropropane was vaporized and was supplied to the reactor at a flow rate of about 0.25 g/min. 1,1,2-trichloro-3,3,3-trifluoropropane was supplied for 3 hours, and 44.5 g thereof was put into the reactor (contact time: 107 seconds). The temperature of the reactor during this period was higher than or equal to 240° C. and lower than or equal to 250° C. Generated gas flowing out from the reactor was caused to flow into a water-containing gas washing bottle formed of a fluorine resin that had been cooled in an iced water bath. Thus, hydrogen chloride was absorbed and the reaction product was collected. 33.4 g of organic substance that was collected and analyzed by gas chromatography to find the following composition ratio. The organic substance contained 1,2-dichloro-3,3,3-trifluoropropene at a content of 97.82% (in more detail, cis-1,2-dichloro-3,3,3-trifluoropropene was contained at a content of 92.74%, and trans-1,2-dichloro-3,3,3-trifluoropropene was contained at a content of 5.08%). The yield of 1,2-dichloro-3,3,3-trifluoropropene was 91.4%.

TABLE 1

| Catalyst | | Reaction temperature (° C.) | Contact time (s) | Composition ratio of product (GC surface area) | | |
|---|---|---|---|---|---|---|
| | | | | 1223xd (Z) | 1223xd (E) | 233da |
| Example 1 | Activated carbon | 250 | 107 | 92.74 | 5.08 | 0.02 |

1223xd (Z): cis-1,2-dichloro-3,3,3-trifluoropropene
1223xd (E): trans-1,2-dichloro-3,3,3-trifluoropropene
233da: 1,1,2-trichloro-3,3,3-trifluoropropane As described in Japanese Laid-Open Patent Publication No. 2012-20992 mentioned above, it is known that 1,2-dichloro-3,3,3-trifluoropropene (1223xd) is generated by a fluorination reaction and a dehalogenation reaction of a chlorine-containing compound such as 1,1,1,3,3-pentachloropropane or the like in a vapor phase in the absence of a catalyst. However, 1,2-dichloro-3,3,3-trifluoropropene (1223xd) obtained by a fluorination reaction and a dehalogenation reaction of a chlorine-containing compound such as 1,1,1,3,3-pentachloropropane or the like in a vapor phase in the absence of a catalyst is in an extremely small amount. 1,2-dichloro-3,3,3-trifluoropropene is not obtained in an industrially sufficient amount by the method described in Japanese Laid-Open Patent Publication No. 2012-20992. As can be seen from a comparison of the results of example 1 against the known method described in Japanese Laid-Open Patent Publication No. 2012-20992, the conversion ratio into 1,2-dichloro-3,3,3-trifluoropropene is higher when the method for producing 1,2-dichloro-3,3,3-trifluoropropene according to the present invention is used.

According to the present invention, 1,2-dichloro-3,3,3-trifluoropropene is produced in an industrial scale at a high yield by use of 1,2-dichloro-1-halogeno-3,3,3-trifluoropropane, which is available at low cost, as a material.

According to the present invention, the amount of generated byproducts, which are not 1,2-dichloro-3,3,3-trifluoropropene as the target compound, is very small. In addition, no byproduct having a boiling point close to that of the target compound is generated. Therefore, the resultant product can be easily purified by distillation or the like, which is a process that is economically advantageous and also has little environmental load.

1,2-dichloro-3,3,3-trifluoropropene, which is a target compound of the present invention, is usable as a heat transfer medium usable for a heat pump cycle or a rankine cycle, a functional material such as a cleaner or the like, a physiologically active substance, an intermediate of a functional material, or a monomer of a polymer compound.

The invention claimed is:

1. A method for producing 1,2-dichloro-3,3,3-trifluoropropene comprising:
putting 1,2-dichloro-1-halogeno-3,3,3-trifluoropropane represented by formula [1] into contact with an activated carbon catalyst in a vapor phase:

[Chemical formula 1]

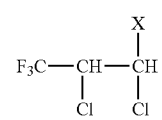

[1]

(in the formula, X represents fluorine, chlorine or bromine).

2. A method according to claim 1, wherein the activated carbon catalyst is formed of activated carbon having no metal material supported thereon.

3. A method according to claim 1, wherein the 1,2-dichloro-1-halogeno-3,3,3-trifluoropropane is in contact with the activated carbon catalyst for a time that is longer than or equal to 1 second and shorter than or equal to 300 seconds, and at a temperature that is higher than or equal to 200° C. and lower than or equal to 350° C.

4. A method according to claim 1, wherein the 1,2-dichloro-1-halogeno-3,3,3-trifluoropropane is 1,1,2-trichloro-3,3,3-trifluoropropane.

* * * * *